United States Patent [19]

Breazeale

[11] Patent Number: 4,581,935

[45] Date of Patent: Apr. 15, 1986

[54] METHOD AND APPARATUS FOR GRADING FIBERS

[75] Inventor: Mack A. Breazeale, Knoxville, Tenn.

[73] Assignee: University of Tennessee Research Corporation, Knoxville, Tenn.

[21] Appl. No.: 686,842

[22] Filed: Dec. 27, 1984

[51] Int. Cl.⁴ ............................................. G01N 29/00
[52] U.S. Cl. ........................................ 73/599; 73/160; 73/602
[58] Field of Search .................. 73/597, 599, 602, 159, 73/160

[56] References Cited

U.S. PATENT DOCUMENTS

| | | | |
|---|---|---|---|
| 2,538,444 | 1/1951 | De Mars | 73/599 |
| 2,966,057 | 12/1960 | Heller | 73/599 |
| 3,486,369 | 12/1969 | Korzilius | 73/580 |
| 3,750,461 | 8/1973 | Felix | 73/597 |
| 3,925,850 | 12/1975 | Lytton | 19/240 |
| 3,984,895 | 10/1976 | Grice, Jr. | 19/240 |
| 4,481,820 | 11/1984 | Thomann | 73/597 |

Primary Examiner—Howard A. Birmiel
Attorney, Agent, or Firm—Luedeka & Neely

[57] ABSTRACT

The specification discloses a method for grading fibers in which a tone burst of sound having a known spatial frequency distribution is transmitted along a sound path through a sample of fibers. After the sound waves have passed through the sample, they are detected, and the detected sound waves are analyzed to determine their spatial frequency distribution which is indicative of the grade of the sample of fibers.

15 Claims, 14 Drawing Figures

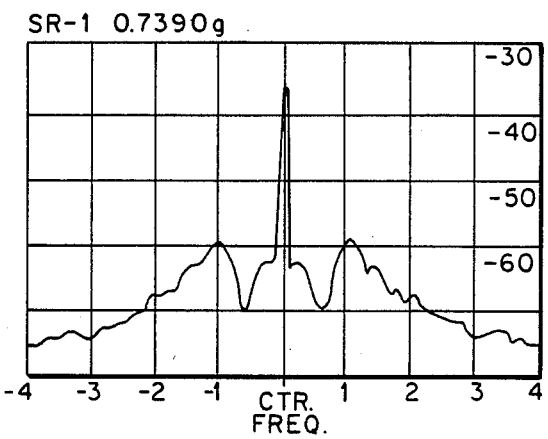
Fig. 3a
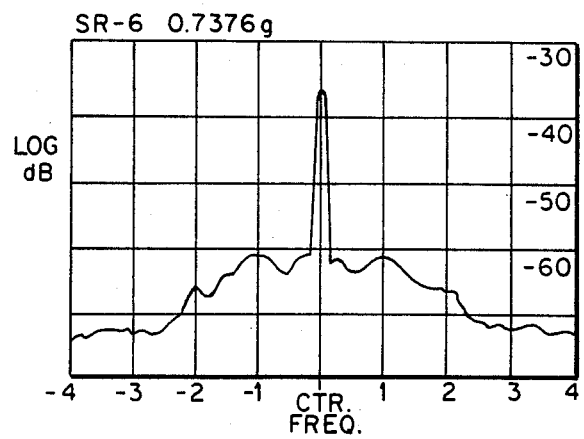
Fig. 3b
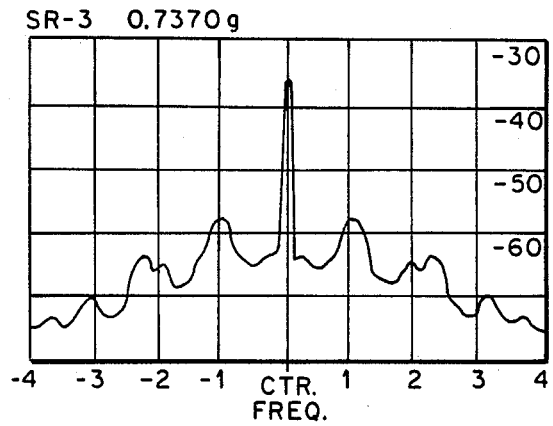
Fig. 3c
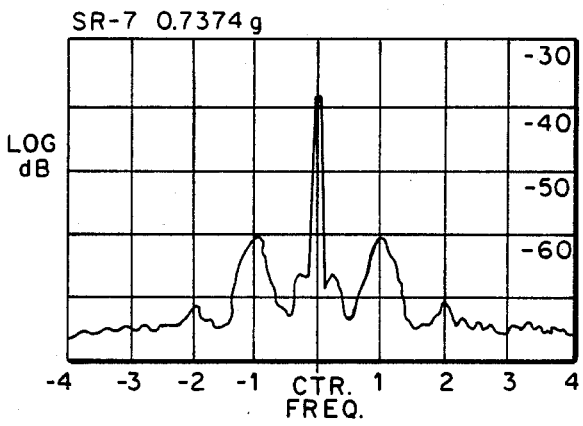
Fig. 3d
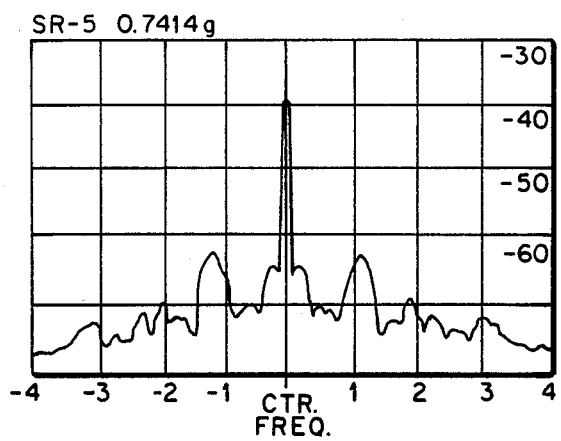
Fig. 3e
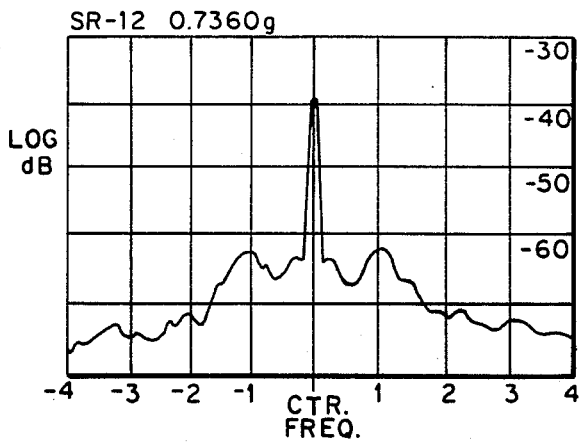
Fig. 3f
Fig. 3

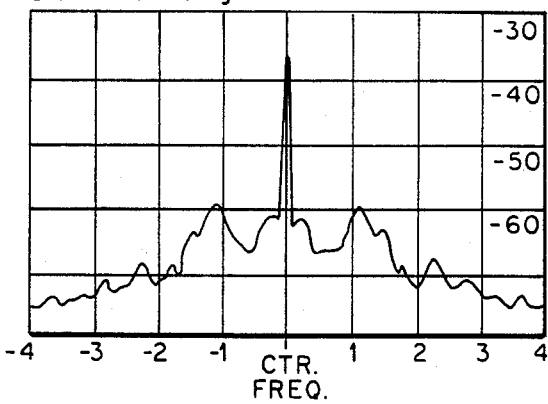
Fig.4a
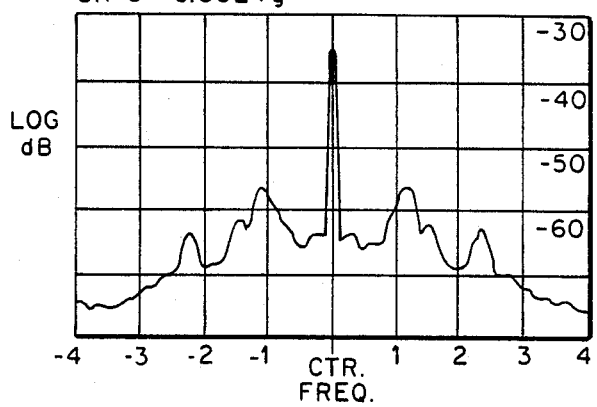
Fig.4b
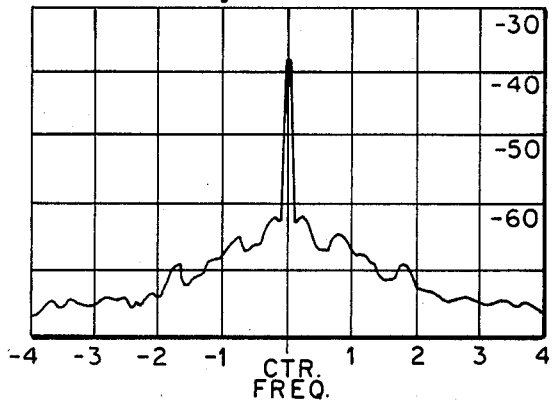
Fig.4c
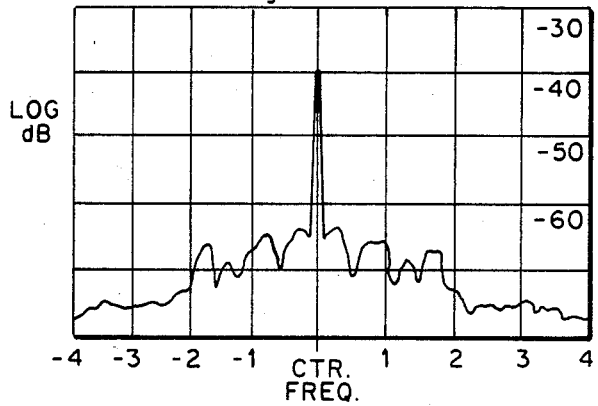
Fig.4d
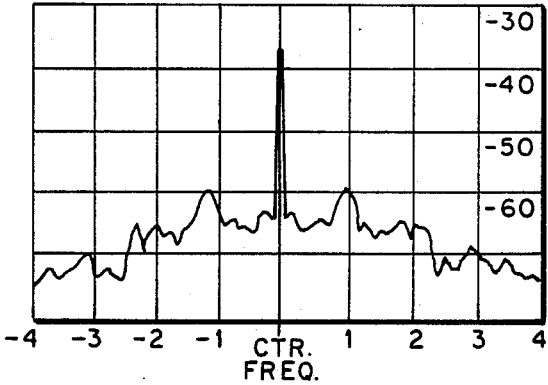
Fig.4e
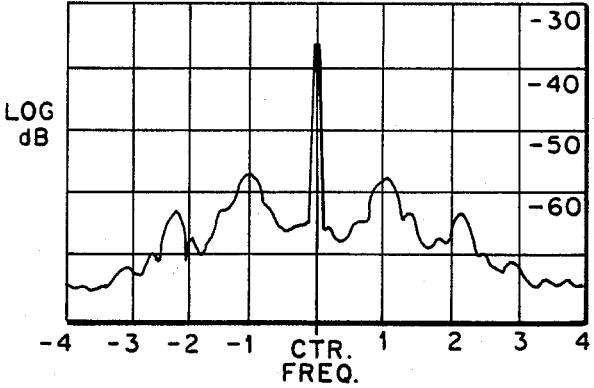
Fig.4f
Fig.4

METHOD AND APPARATUS FOR GRADING FIBERS

METHOD AND APPARATUS FOR GRADING FIBERS

The present invention relates to the grading of fibers and particularly relates to a method and apparatus for grading fibers in which sound waves are directed through a fiber sample and the effect of the fibers on the frequency content of the sound waves is observed.

Fibers, such as cotton, are graded according to a combination of physical characteristics, and the early grading technique was simply a touch and feel method. Fibers were categorized or graded according to how they felt to the human touch. This rather subjective testing technique resulted in a grading system in which standardized grades depended upon a number of fiber characteristics, such as length, fineness, immaturity, tenacity, elongation and toughness, but the standardized grades did not correspond well with any of these physical characteristics. One could not measure one or more of the physical characteristics mentioned above and then use those physical characteristics to easily ascertain the grade of the fiber. It was and is difficult to grade fibers based on these physical characteristics and, thus, it is difficult to remove the subjective element from the grading process.

In response to the need to establish some uniformity in the fiber grading system and to inject some objectivity into this system, Dr. Kenneth L. Hertel of the University of Tennessee extensively analyzed the physical characteristics of the various grades of cotton fibers and discovered that the X-ray forward scattering characteristics of cotton fibers accurately corresponded to the fiber grade. Thus, techniques for grading fibers using X-ray forward scattering techniques were developed. However, these X-ray techniques were relatively expensive from an equipment standpoint, were cumbersome and were somewhat difficult to perform accurately. Also, there are operator health concerns involved with the use of X-rays to grade fibers.

At present, light techniques are also used to grade fibers and typically light is transmitted through a sample and the diffraction effect on the light is observed to determine the grade of the fiber. These light diffraction techniques are not very reliable and the X-ray forward scattering technique of grading fibers remains the most dependable.

The present invention utilizes sound waves to grade fibers. Sound and particularly ultrasonic sound have been used in numerous devices to determine various physical characteristics of materials, but these known devices do not disclose or use a method for determining a grade of fibers. For example, U.S. Pat. Nos. 2,966,057 and 2,538,444 disclose systems that measure attenuation of ultrasonic energy when it passes through a medium. Using this technique, imperfections in yarn may be detected, for example. U.S. Pat. No. 3,750,461 discloses a system using sound waves to determine the cross-section of yarn. In this patent, it is disclosed that disturbances of standing soundwaves may be observed to determine the cross-section of yarn. Also, U.S. Pat. Nos. 3,984,895, and 3,925,850 each disclose an apparatus for determining the density of textile products and, again, these devices measure attenuation of continuous ultrasonic signals to measure density. The devices disclosed in the above discussed patents measure certain physical characteristics of materials, but there is no suggestion in these patents that the measurements could be used in grading fibers and, in fact, the measurements taken by these devices would not be very useful for such purpose.

In accordance with the present invention, an apparatus and method are provided in which fibers are graded by observing the frequency content of sound, preferably ultrasonic sound, after it passes through a sample of fibers. It has been discovered that the effect of fibers in altering the frequency content of sound waves corresponds well to the fiber grades and, thus, is a reliable indication of the grade of a fiber sample. In order to grade fibers in accordance with the method of the present invention, a sample of fibers is disposed in a sound path and sound waves are transmitted along the sound path through the fibers. The transmitted sound waves have more than one frequency component and the effect of the sample on the sound waves varies with frequency. The sound waves are detected after they have passed through the sample and the frequency content of the detected sound waves is determined. This frequency content is indicative of the grade of the sample of fibers.

In the preferred embodiment of the present invention, at least one sound tone burst having a known spatial frequency distribution about a single selected frequency is produced. This spatial frequency distribution is a natural phenomenon that will occur when the tone burst is created. After the tone burst has travelled through the sample, the spatial frequency distribution of the tone burst is determined and such distribution will indicate the grade of the particular sample. By comparing the spatial frequency distribution of the detected sound waves with known spatial frequency distributions corresponding to known grades of fiber, it is possible to determine which known spatial frequency distribution most closely corresponds to the spatial frequency distribution of the detected sound wave. In this manner, by comparing frequency distributions, it is possible to grade the sample.

In the preferred embodiment, the tone bursts are produced having a predetermined time duration and are transmitted at predetermined time intervals. The duration of the tone burst is chosen to be sufficiently short so that the entire tone burst is detected before any echo from the tone burst can be detected. Also, the time interval between two tone bursts is sufficiently long to allow echos from one tone burst to dissipate before another tone burst is transmitted.

In order to facilitate the determination of the spatial frequency distribution of a received sound wave, a gating technique is utilized so that substantially only meaningful signals are analyzed. In order to accomplish the gating, an electrical pulse at a selected frequency and a synchronizing spike are simultaneously generated. The electrical pulse at the selected frequency is used to produce a tone burst of sound and that tone burst will have a spatial frequency distribution about the selected frequency. The tone burst is transmitted through the sample of fibers and is received after it passes through the sample. The received tone burst is then converted into an electrical received signal. Since sound travels at a relatively slow speed compared to electrical signals, in order to maintain synchronization, a delayed synchronizing pulse is produced. This delay corresponds to the time period between the transmission of the tone burst and the receiving of the tone burst. The electrical received signal is gated in response to the delayed synchronizing pulse to produce a gated received signal which corresponds to the electrical received signal for a selected time period after the production of the delayed synchronizing pulse. The selected time period of the gate is chosen so that a time window opens only when meaningful signals are present. That is, a gate opens and passes the received signal corresponding to a tone burst, but between tone bursts, the gate is closed to block out noise. The gated received signal is then analyzed to determine the spatial frequency distribution thereof which, in turn, will correspond to the grade of the sample fibers.

The present invention may best be understood by reference to the following detailed description of a preferred embodiment when considered in conjunction with the drawings in which:

FIGS. 3a–3f are graphs of spatial frequency distributions produced by sound passing through six different cotton fiber samples, each sample having a weight of about 0.738 grams; and FIGS. 4a–4f are graphs of spatial frequency distributions produced by sound passing through six different grades of cotton fiber samples, each sample having a weight of about 0.365 grams.

Figure 1:
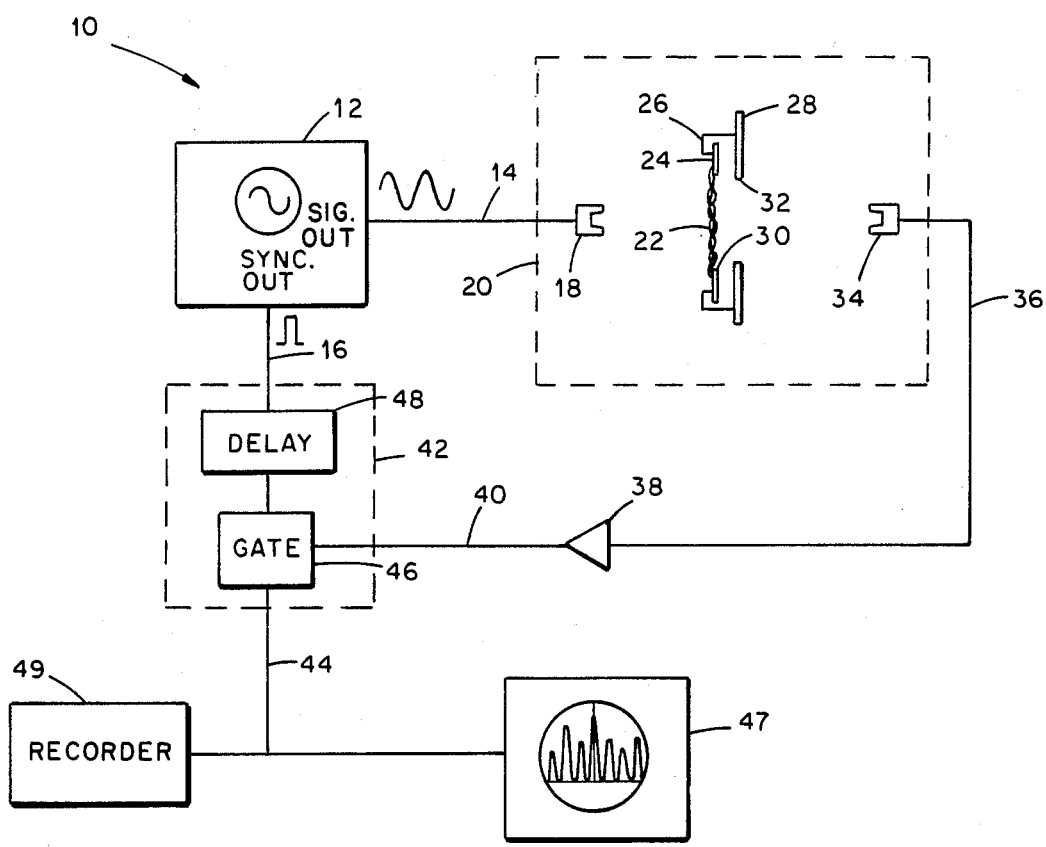
FIG. 1 is a circuit diagram of an apparatus embodying one form of the present invention.

Referring now to the drawings in which like reference characters designate like or corresponding parts throughout the several views, there is shown in FIG. 1 a schematic diagram 10 representing one form of the present invention. The diagram 10 includes a pulse modulator 12 that generates an A.C. electrical pulse at a frequency of one megahertz on line 14 and also generates a synchronization spike on ine 16. In this particular embodiment, a Matec Model No. 6600 pulse modulator 12 is used. As used herein, the term "pulse" refers to an alternating current over a finite period of time. The time length of the pulse produced by the pulse modulator 12 is approximately one tenth (0.1) of a millisecond and the repetition rate of the pulses is approximately one hundred (100) pulses per second so that the interval between pulses is approximately one hundredth (0.01) of a second.

Line 14 is connected to a source transducer 18 for producing ultrasonic sound. In this particular embodiment a barium-titanate ceramic transducer is used, but it will be understood that other sound transducers may be used. The transducer 18 produces an ultrasonic tone burst in response to the electrical signal received on line 14. The tone burst has a duration of approximately of one-tenth (0.1) of a millisecond and has a repetition of approximately one hundred (100) bursts per second. The one megahertz frequency, the 0.1 millisecond duration and the 100 pulses per second repetition rate work well with the particular equipment used in this embodiment, but they are not considered to be optimum. Also, although ultrasonic "sound" having a frequency of one megahertz is used in the described embodiment, the term "sound", as used herein, will be understood in its broadest sense to include frequencies above, below and within audible ranges.

Figure 2:
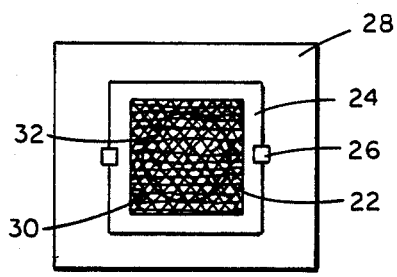
FIG. 2 is a detailed view of the cotton fiber sample and a holder plate.

The source transducer 18 is contained within a housing 20 whose function is to isolate the transducer 18 and other equipment therein from air current and spurious echos and sounds. Also disposed within the housing 20 is a cotton fiber sample 22 that is mounted on a sample board 24 which is mounted by a clamp 26 to a holder plate 28, all of which are also shown in FIG. 2. The sample board 24 includes an aperture 30 over which the sample 22 is disposed, and the holder plate 28 also includes an aperture 32 positioned adjacent to the aperture 30 in the sample board. A receiving transducer 34 is positioned on the other side of the housing 20 from the source transducer 18, and the sample 22 is positioned so that the sound beam produced by the transducer 18 will travel through the cotton fiber sample 22 and will be received by the receiving transducer 34. In this embodiment, the receiving transducer 34 is identical to the source transducer 18, and the two transducers are positioned apart at a distance of approximately one meter. The sample 22 is disposed half way between the two transducers 18 and 34 and the sound beam produced by the transducer 18 is approximately 25 millimeters in diameter. As best shown in FIG. 2, the aperture 32 in the holder plate 28 is approximately 50 millimeters in diameter and the aperture 30 in the sample board 24 is a square with sides of greater than 50 millimeters. Thus, it will be appreciated that the aperture 32 does not intercept the sound beam produced by the source transducer 18, but it merely serves as a holder for the sample 22. Of course, the distances between the transducers and the sizes of the sound beam and apertures may be varied.

The sound signal received by the transducer 34 is converted to an electrical signal and is applied through line 36 to an amplifier 38. The output of the amplifier 38 is applied through line 40 to a stepless gate 42, whose function is to gate the received signal so that it is transmitted to an output line 44 only during selected time intervals. These time intervals are chosen so that the signal on line 44 corresponds only to signals received from the transducer 34 that correspond to the reception of the one megahertz tone burst. Thus, the gate 42 is open for slightly greater than one-tenth of a millisecond and has a repetition rate of one hundred cycles per second. The stepless gate 42 is synchronized with the local pulse modulator 12, but the function of the gate 42 must be delayed slightly to compensate for the time required for the sound to travel from the source transducer 18 to the receiving transducer 34. Thus, gate 42 includes a delay 48 and a gate 46. The delay 48 receives a synchronization spike on line 16 from the local pulse modulator 12 and delays for a predetermined time period after which the delay 48 causes the gate 46 to open for a time period slightly greater than a tenth of a millisecond. In this particular embodiment, the delay period of delay 48 is equal to the time required for sound to travel the one meter from the source transducer 18 to the receiving transducer 34. Since the transducers 18 and 34 are about one meter apart, the delay time of the delay 48 is approximately three milliseconds. Of course, this delay must be adjusted depending upon the distance between the transducers 18 and 34 and the atmospheric conditions prevailing at the particular time of operation. This adjustment may be accomplished by simply looking at the signal on the output line 44 with an oscilloscope and adjusting the delay 48 until the proper signal is seen on the output line 44.

In this particular embodiment, the stepless gate 42 is manufactured by Panametrics (Model 5052G).

The output of the stepless gate 42 is applied through line 44 to a spectrum analyzer 47 that will analyze the signal to determine its spatial frequency distribution. In this particular embodiment, a Hewlett-Packard Spectrum Analyzer Model No. 141S is used as the spectrum analyzer 47. The analyzer 47 will display a graph corresponding to the spatial frequency distribution of the signal received on line 44 with the x-axis corresponding to the frequency and the y-axis corresponding to signal amplitude. The center frequency in this particular embodiment has been chosen to be one megahertz and the spectrum width that is displayed on the screen of the spectrum analyzer 47 is two hundred kilohertz, one hundred kilohertz on either side of the center frequency. The signal on line 44 may also be applied to a recorder 88 which may be a conventional magnetic tape type recorder, or other conventional recorder, which will record the output appearing on line 44 for subsequent analysis.

The spatial frequency distribution shown on the screen of the analyzer 47 is an indication of the grade of the fiber sample 42. The transducer 18 produces a sound wave having a center frequency of one megahertz and whose frequency distribution about one megahertz is defined by the formula of sine X divided by X. As the sound wave passes through the fiber 22, its frequency distribution will be changed because the scattering caused by the fiber sample 22 is a highly frequency dependent phenomenon. That is, the cotton fiber sample 22 will scatter out a part of the sound wave depending upon its particular frequency. Which part or which frequency is scattered out depends upon the physical characteristics of the fiber, and it has been discovered that the scattering effect on the spatial frequency distribution of the sound wave corresponds to the grade of a particular fiber sample. Thus, the frequency content of the tone burst after it passes through the fiber sample 22 may be used to identify the grade of the sample 22. In other words, a particular grade of fiber will have a unique scattering effect on the sound transmitted through it. This unique scattering effect will create a unique spatial frequency distribution in the signal produced by the transducer 34 and displayed by the analyzer 47.

The uniqueness of the spatial frequency distribution of particular samples of cotton fibers may be observed by reference to FIGS. 3 and 4. FIG. 3 shows the spatial frequency distribution for six different grades of cotton fiber where the sample weight is about 0.738 grams. FIG. 4 also shows the spatial frequency distribution for six different grades of fibers where the weight of the sample is 0.365 grams. In both FIGS. 3 and 4 the center frequency is one megahertz and the frequency range across the graph is 200 kilohertz.

In both FIGS. 3 and 4, the grade of the fiber used to create the spatial frequency distribution graph is indicated thereon by the number which begins with "SR", and the precise weight in grams of each sample is indicated on the graphs by the four decimal place number followed by the letter "g". The table below shows the common variety name of the "SR" samples and various other physical characteristics of the samples. This table shows ten different grades of fibers, but graphs for only six representative grades are shown in FIGS. 3 and 4.

| | COTTON FIBER PROPERTIES | | | | | | | |
|---|---|---|---|---|---|---|---|---|
| | Length 2.5% | Fineness | Immaturity | Tenacity ⅛" | Elongation | Toughness | Xray angle | |
| Code Variety | Span in. | A mm$^{-1}$ | D mm$^{-1}$ | Gauge g/tex | % | $T_1E_1/2$ g/tex | 40% degree | 50% degree |
| SR-1 | 1.13 | 463 | 44 | 18.7 | 8.1 | .76 | 34.9 | 31.8 |
| SR-2 Deltapine Smooth Leaf | 1.15 | 458 | 35 | 19.1 | 9.0 | .86 | 38.2 | 34.7 |
| SR-3 Stoneville 3202 | 1.06 | 512 | 50 | 16.7 | 7.7 | .64 | 35.9 | 32.5 |
| SR-4 Stoneville 7A | 1.15 | 488 | 46 | 17.6 | 7.3 | .64 | 34.9 | 31.9 |
| SR-5 Rex | 1.02 | 543 | 58 | 16.9 | 8.1 | .68 | 37.4 | 33.8 |
| SR-6 Lankart 57 | .99 | 552 | 64 | 16.4 | 8.7 | .71 | 40.6 | 36.7 |
| SR-7 Cal 7-8 | 1.07 | 446 | 28 | 22.1 | 6.2 | .69 | 29.9 | 26.6 |
| SR-8 Acala 4-42 | 1.11 | 516 | 48 | 21.8 | 7.8 | .85 | 33.5 | 30.2 |
| SR-12 Acala 1517V | 1.19 | 474 | 31 | 22.2 | 7.3 | .81 | 31.1 | 27.9 |
| SR-13 Pima S-2 | 1.36 | 495 | 34 | 30.3 | 9.0 | 1.37 | 29.8 | 26.9 |

By comparing the six graphs shown in FIG. 3, one to the other, it will be appreciated that each grade of fiber at a particular weight of sample creates a spatial frequency distribution that is distinct from the spatial frequency distributions of the other grades of fibers. Likewise, reference to FIG. 4 shows that at a different sample weight, the various grades of fibers continue to create unique spatial frequency distributions.

One method of grading fibers utilizing the method of the present invention would be to first determine and record the spatial frequency distributions of numerous known grades of fibers at a particular sample weight. For example, the graphs shown in FIG. 3 represent spatial frequency distributions for six known grades of fiber at a known sample weight. Next, a sample would be prepared from an unknown grade of cotton fibers. This sample would be weighed so that it had the same weight as the known grades. For example, if the spatial frequency distributions of FIG. 3 were being used, the sample of the unknown fibers would be prepared to have a weight of about 0.738 grams. This sample would be placed on a sample board 24 and mounted on the holder plate 28 using the apparatus shown in FIG. 1, and the spatial frequency distribution of the unknown sample could be determined by simply viewing the screen of the analyzer 47. Then by visually comparing the spatial frequency distributions shown on the screen of the analyzer 47 with the graphs of the spatial frequency distributions for known grades of fiber, one could determine the grade of the unknown fiber by matching its spatial frequency distribution to the spatial frequency distribution of one known grade of fiber. Once an operator became skilled, he could grade the fiber by simply reading the spatial frequency distribution much like a physician reads an electrocardiogram, an X-ray or the like.

Of course, this visual comparison technique is a somewhat subjective pattern recognition technique and the accuracy of the grading would depend to some extent on the skill of the operator and his ability to match the spatial frequency distribution of the unknown samples to the spatial frequency distribution of a particular grade of fibers. This subjective element could be eliminated by using computer pattern recognition techniques. In this contemplated process, the known spatial frequency distribution of known fiber grades would be placed in the memory of a computer and the spatial frequency distribution of an unknown sample would be input into the computer. The computer would use pattern recognition techniques to determine the best match between the unknown sample and the spatial frequency distributions of the known grades of fibers stored in memory.

It is also contemplated that analog techniques could be used to directly perform the comparison described above. For example, the output signal appearing on line 44 shown in FIG. 1 could be recorded for each of the known grades of fiber at a particular sample weight. Then, an unknown grade of fiber could be used as the sample 22 and the electrical signal produced on line 44 by the unknown sample could be directly compared with the recorded signals to find the best match using analog comparison techniques.

While most of the operating characteristics of the present invention are not critical, the selection of the operating parameters should be within certain ranges to achieve optimum performance. In the embodiment described above, the pulse produced by the local pulse modulator 12 and the tone burst produced by transducer 18 has a duration of 0.1 milliseconds. Thus, the tone burst produced by the transducer 18 will have a length of approximately 33 millimeters. This tone burst will pass through the cotton fiber sample 22 and will be received by the transducer 34. The leading edge of the tone burst will be reflected, partially, by the transducer 34 in numerous directions and particularly back toward the plate 28. In order to avoid echo problems, the length of the tone burst should be less than twice the length from the receiving transducer 34 to the nearest object. In the embodiment shown in FIG. 1, the nearest object is the plate 28 which is positioned at a distance of approximately five hundred millimeters from the receiving transducer 34. Of course, there could be other sources of echos. For example, sound waves could be reflected back from the sample 22, the sample board 24, and the plate 28 toward the transducer 18 and then reflected from the transducer 18 back toward the transducer 34. In order to avoid all of these echo problems, the length of the tone burst, thirty-three millimeters was chosen to be significantly smaller than the distance between the transducer 34 and the plate 28 so that the potential for echo problems would be minimized. When the echos are being received by the transducer 34, the stepless gate 42 will be turned "off" so that the signal produced by the transducer 34 will not be transmitted to the analyzer 47.

Likewise, the repetition rate of the tone bursts from the transducer 18 is important. By allowing approximately 0.01 seconds between tone bursts, there is sufficient time for the energy of one tone burst to dissipate to an acceptably low noise level before the next succeeding tone burst is produced. In this manner, echos from one tone burst will not interfere with the reception of another tone burst by the receiving transducer 34.

While a particular embodiment of the invention has been described above, it will be appreciated that the invention is capable of numerous rearrangements, modifications and substitutions without departing from the spirit of the invention. In particular, it should be noted that the analysis of the spatial frequency distribution of the tone bursts received by transducer 34 may be accomplished in a number of fashions. Perhaps the easiest is a visual comparison of the spatial frequency distribution of an unknown sample of fibers with graphs of the spatial frequency distributions of known grades of fibers. The key to the analysis is the recognition of the fact that the fibers will generate a signal at the receiving transducer 34 having frequency information that is indicative of the grade of the sample fibers.

What is claimed is:

1. A method for grading fibers, comprising:
    disposing a sample of fibers of an unknown grade in a sound path;
    transmitting sound waves along the sound path through the sample of fibers, said sound waves having more than one frequency component;
    detecting the sound waves after they have passed through the sample; and
    analyzing the frequency content of the detected sound waves to determine the grade of the sample of fibers.

2. The method of claim 1 wherein said transmitting step comprises transmitting a plurality of tone bursts along the sound path, said tone bursts having predetermined time durations and being transmitted at predetermined time intervals, said durations of of tone bursts being sufficiently short so that an entire tone burst is detected before any echo from the tone burst can be detected, said time interval between tone bursts being sufficiently long to allow echos from one tone burst to substantially dissipate before another tone burst is transmitted.

3. The method of claim 1 wherein:
    said transmitting step comprises transmitting at least one tone burst having a known spatial frequency distribution about a selected frequency; and
    said analyzing step comprises determining the spatial frequency distribution of said tone burst after said tone burst has travelled through the sample.

4. The method of claim 1 further comprising:
    disposing at least one sample of fibers of a known grade in a sound path;
    transmitting sound waves along the sound path through the fiber sample of a known grade, said sound waves having more than one frequency component;
    detecting the sound waves after they have passed through the fiber sample of a known grade; and
    comparing the frequency content of the detected sound waves corresponding to the known grade of fibers with the frequency content of the detected sound waves corresponding to the unknown grade of fibers to determine the degree of similarity between the two frequency contents.

5. The method of claim 1 wherein said steps of transmitting and analyzing comprise:
    generating simultaneously an electrical pulse at a selected frequency and a synchronizing spike;

producing a tone burst of sound at the selected frequency in response to the electrical pulse, said tone burst having a spatial frequency distribution about said selected frequency;

transmitting said tone burst through the sample of fibers;

receiving the tone burst after it passes through the sample and converting the received tone burst into an electrical received signal;

producing a delayed synchronizing spike at a predetermined delay after said synchronizing spike, said delay corresponding to the time period between the steps of transmitting the tone burst and receiving the tone burst; and determining the spatial frequency distribution of the received signal in response to the delayed synchronizing spike.

6. The method of claim 1 wherein said steps of transmitting and analyzing comprise:

generating simultaneously an electrical pulse at a selected frequency and a synchronizing spike;

producing a tone burst of sound at the selected frequency in response to the electrical pulse, said tone burst having a spatial frequency distribution about said selected frequency;

transmitting said tone burst through the sample of fibers;

receiving the tone burst after it passes through the sample and converting the received tone burst into an electrical received signal;

producing a delayed synchronizing spike at a predetermined delay after said synchronizing spike, said delay corresponding to the time period between transmitting the tone burst and receiving the tone burst;

gating the received signal in response to the delayed synchronizing spike to produce a gated received signal that corresponds to the received signal for a selected time period after the production of the delayed synchronizing spike; and analyzing the gated received signal and determining the spatial frequency distribution of the gated received signal to thereby determine the grade of the sample fibers.

7. An apparatus for grading a sample of fibers, comprising:

a holder for disposing a sample of fibers in a sound path;

transmitting means for generating and transmitting sound waves along the sound path and through the sample of fibers;

a detector for detecting the sound waves after the sound waves have passed through the sample and for generating a detection signal corresponding to the detected sound waves; and means for analyzing the frequency content of the detection signal to determine the grade of the sample of fibers.

8. The apparatus of claim 7 wherein said transmitting means comprises:

a pulsed oscillator for generating a plurality of frequency pulses, said pulses being generated at a selected frequency, a selected duration and a selected repetition rate with a selected interval between the beginning of each pulse;

a source transducer connected to said pulsed oscillator for producing tone bursts of sound in response to said frequency pulses, said tone bursts having spatial frequency distributions about said selected frequency and having the selected duration and the selected interval between the beginning of each tone burst; and the selected duration of each tone burst being sufficiently short in time so that the entire tone burst is received at said detector before any echo of the tone burst can reach said detector and said selected interval being sufficiently long in time so that the echos of a tone burst are substantially dissipated before the next tone burst is produced.

9. The apparatus of claim 8 wherein said oscillator produces a pulse having a selected duration that is sufficiently short so that the length of the tone burst in distance is less than twice the distance between said detector and any nearest object.

10. The apparatus of claim 8 wherein said pulsed oscillator produces a pulse having a selected duration that is sufficiently short so that the length of the tone burst in distance is less than twice the distance between the sample and said detector.

11. The apparatus of claim 8 wherein said means for analyzing comprises spatial frequency analyzer means for determining and displaying the spatial frequency distribution of the detection signal.

12. The apparatus of claim 7 wherein said transmitting and analyzing means comprise:

a pulsed oscillator for generating a plurality of electrical pulses at a selected frequency, said pulses being generated for a selected duration and at a selected repetition rate with a selected interval between the beginning of each pulse;

said pulse oscillator also generating a synchronizing spike at the start of said pulse;

a source transducer connected to said pulsed oscillator for producing tone bursts of sound in response to said pulses, said tone bursts having a spatial frequency distribution about said selected frequency and having the selected duration and the selected interval between the beginning of each tone burst;

the selected duration being sufficiently short in time so that the entire tone burst is received at said detector before any echo of the tone burst can reach said detector and said selected interval being sufficiently long in time so that the echos of one tone burst are substantially dissipated before the next tone burst is produced;

a stepless gate connected to selectively transmit the detection signal from said detector to an output of said stepless gate in response to said synchronizing spike, said stepless gate being operable to remain open for transmitting the detection signal for a predetermined time period in response to said synchronizing spike;

said stepless gate including an internal delay that delays the opening of said stepless gate for a delay period corresponding to the time required for sound to travel from said source transducer to said detector so that in response to said synchronization spike said stepless gate delays for the delay period and then opens for a predetermined time period to transmit the detection signal to an output; and a spatial frequency analyzer connected to the output of said stepless gate for determining the frequency distribution of the detection signal.

13. The apparatus of claim 12 wherein said spatial frequency analyzer is operable to display a graph corresponding to the spatial frequency distribution of the detection signal.

14. The apparatus of claim 12 wherein said pulsed oscillator produces a pulse for a selected duration that is sufficiently short in time so that the length of the tone burst in distance is less than twice the distance between said detector and any nearest object.

15. The apparatus of claim 12 wherein said pulsed oscillator is operable to produce a frequency pulse having a center frequency of about one megahertz.

* * * * *